Figure 1:
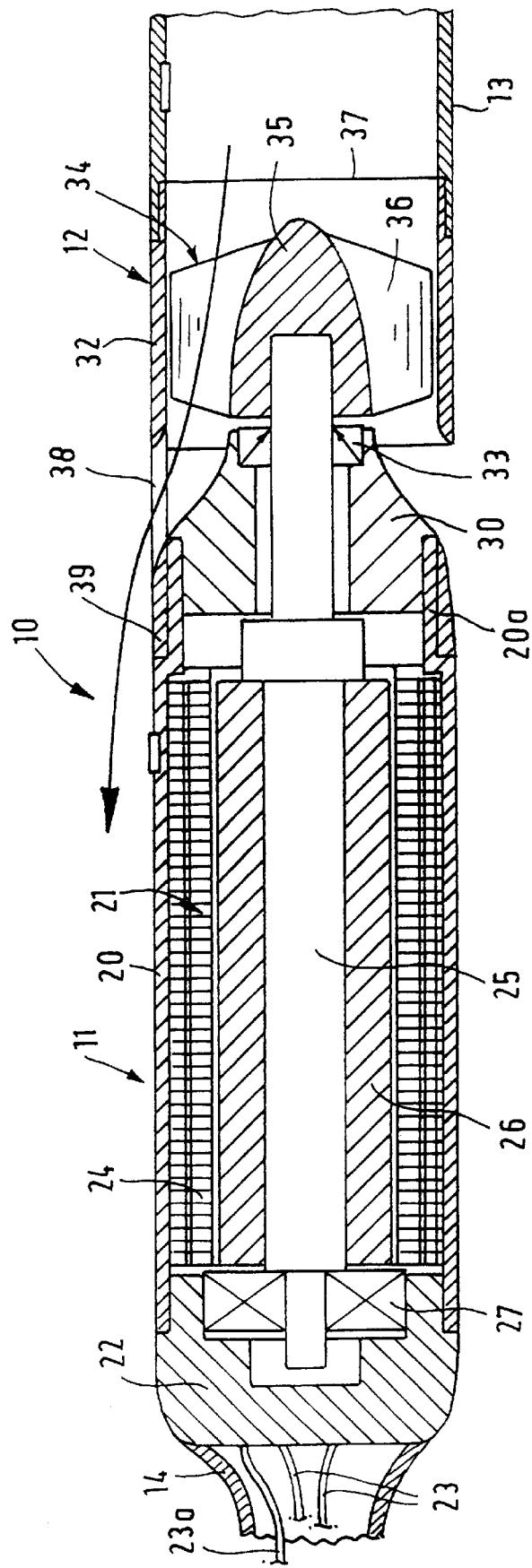

United States Patent
Siess

[11] Patent Number: 6,139,487
[45] Date of Patent: Oct. 31, 2000

[54] INTRACARDIAC PUMP DEVICE

[75] Inventor: Thorsten Siess, Wuerselen, Germany

[73] Assignee: Impella Cardiotechnik AG, Aachen, Germany

[21] Appl. No.: 09/194,725

[22] PCT Filed: Mar. 31, 1998

[86] PCT No.: PCT/EP98/01868

§ 371 Date: Dec. 2, 1998

§ 102(e) Date: Dec. 2, 1998

[87] PCT Pub. No.: WO98/43689

PCT Pub. Date: Oct. 8, 1998

Related U.S. Application Data

[63] Continuation-in-part of application No. 08/832,040, Apr. 2, 1997, Pat. No. 5,911,685.

[51] Int. Cl.[7] ...................................................... A61M 1/12
[52] U.S. Cl. .................................. 600/16; 623/3; 415/900
[58] Field of Search ............................ 600/16, 17; 623/3; 415/900, 229, 230

[56] References Cited

U.S. PATENT DOCUMENTS

| | | |
|---|---|---|
| 3,568,659 | 3/1971 | Karnegis . |
| 4,382,199 | 5/1983 | Isaacson . |
| 4,625,712 | 12/1986 | Wampler .................................. 600/16 |
| 4,688,998 | 8/1987 | Olsen et al. . |
| 4,704,121 | 11/1987 | Moise . |
| 4,779,614 | 10/1988 | Moise . |
| 4,817,586 | 4/1989 | Wampler . |
| 4,846,152 | 7/1989 | Wampler et al. . |
| 4,895,557 | 1/1990 | Moise et al. . |
| 4,906,229 | 3/1990 | Wampler . |
| 4,908,012 | 3/1990 | Moise et al. . |
| 4,919,647 | 4/1990 | Nash . |
| 4,944,722 | 7/1990 | Carriker et al. . |
| 5,061,256 | 10/1991 | Wampler . |
| 5,092,879 | 3/1992 | Jarvik . |
| 5,112,292 | 5/1992 | Hwang et al. . |
| 5,376,114 | 12/1994 | Jarvik . |
| 5,385,454 | 1/1995 | Kopbayashi et al. . |
| 5,385,581 | 1/1995 | Bramm et al. . |
| 5,393,207 | 2/1995 | Maher et al. . |
| 5,507,629 | 4/1996 | Jarvik . |
| 5,527,159 | 6/1996 | Bozeman, Jr. et al. . |
| 5,695,471 | 12/1997 | Wampler . |
| 5,911,685 | 6/1999 | Siess et al. . |
| 5,921,913 | 7/1999 | Siess . |
| 5,964,694 | 10/1999 | Siess et al. . |

FOREIGN PATENT DOCUMENTS

| | | |
|---|---|---|
| 2113986 | 3/1971 | Germany . |
| PCT/US93/ 09947 | 10/1993 | WIPO . |

*Primary Examiner*—Jeffrey R. Jastrzab
*Attorney, Agent, or Firm*—Fulwider Patton Lee & Utecht, LLP

[57] ABSTRACT

The pump device comprises a first pump (10*a*) that may have its intake side inserted into the left ventricle (42) of the heart, while the delivery side is located in the aorta (40), and a second pump (10*b*) having its intake side arranged in the right atrium (43), whereas its delivery side is in the pulmonary artery (47). A common control unit drives both pumps in mutual dependance, the first pump (10*a*) taking the lead function, whereas the second pump (10*b*) pumps only about 90% of the volume flow of the first pump (10*a*). Pressure sensors at the pumps serve to determine the differential pressure between the intake side and the delivery side of a pump and to determine the volume flow. Both pumps are inserted into the heart without having to open the ventricles.

13 Claims, 5 Drawing Sheets

INTRACARDIAC PUMP DEVICE

This application is a continuation-in-part of U.S. patent application Ser. No. 08/832,040 filed Apr. 2, 1997, which issued as U.S. Pat. No. 5,911,685.

The invention relates to an intracardiac pump device with two pumps that may be inserted into the heart to assist the natural cardiac pump function or to replace the same by a continuous pumping operation.

A pump device for supporting the heart is described in WO94/09835 (Jarvik). This pump device comprises two independent pumps each having a pump portion and a drive portion rigidly connected therewith. The pump portion of the one pump is introduced into the left ventricle through an operation opening at the apex of the heart such that it delivers blood from the left ventricle into the aorta. The other pump portion is introduced through another operation opening into the right ventricle such that it delivers blood from the right ventricle into the pulmonary artery. The system further comprises a control and display module that is small enough to be sterilized and used in the sterile environment of the operation. It may include a microprocessor with control and monitoring algorithms for regulating the volume flow and the pressure, or to supply the volume flow and the pressure to a data base, the values thereof having bee n measured by sensors or having been calculated by comparing the measurements of velocity and energy consumption. These pumps, referred to as cannula pumps, may be equipped with built-in pressure sensors or volume flow measuring devices to take local measurements of these parameters in the context of patient management.

It is an object of the present invention to provide an intracardiac pump device with at least two pumps that allows to achieve an effective support of the heart by suitably determining the operational conditions of both pumps.

The present intracardiac pump device comprises two pumps to be placed in the heart, each having a drive portion and a pump portion rigidly connected thereto. Both pumps are driven in mutual dependance by a common control means. According to the present invention, the two pumps are not driven independently but such that in both pumps the parameters important for the operation of the pump are adapted to each other. Thus, any interfering operation of both pumps is avoided and, further, the occurrence of unnatural pressure or suction conditions in the heart and the peripheral organs is prevented.

In the context of the present invention, the term "intracardiac" is meant to refer to the ventricles, the vestibules and the adjacent vascular stumps.

An essential parameter of an intracardiac blood pump is the volume flow conveyed per unit of time. The controls of both pumps are tuned to each other such that the volume flows are in a predetermined relation to each other. When one pump is used as a right heart pump and the other is used as a left heart pump, both pumps deliver into fluid systems that, seen in the flow direction, are arranged in series behind each other, with the supply system to the lung being flown through first, this system being in direct fluid communication with the right ventricle. After oxygenation of the blood in the lung, the blood returns to the heart, i.e. to the left ventricle. From the left ventricle, the blood is pumped into the aorta. In the peripheral vessel system, however, the volume of blood is reduced by about 10% due to branches and "leakages". The volume flow of the right heart pump is smaller by a predetermined percentage, preferably about 10%, than that of the left heart pump. This fixed percentage remains the same in case of a variation in the volume flow, i.e. the volume flows of both pumps change in the same percentage amount.

The common control unit of both pumps may also comprise different control means communicating with each other so that a change in the volume flow of one pump automatically causes a corresponding change of the volume flow of the other pump.

Preferably, both pumps are operated under master-slave control, the left heart pump usually taking the function of the master. The left heart pump is the pump that has to deliver the largest output volume against the highest counter-pressure, which is why it is subjected to the greatest workload.

Both pumps may have the same design and, thus, may have the same structure and operational characteristics.

Preferably, the pumps are designed as intravascular pumps as described in WO97/37696 (published posteriorly). Such an intravascular blood pump is connected to a catheter. It is small enough to be pushed through a blood vessel to the place where it is intended to work, or it may also be operated in the blood vessel. In an intravascular blood pump of this type, the pump portion and the drive portion have substantially the same diameter of no more than about 5–7 mm, since the vessel width in peripheral regions of the body is slightly larger than 7 mm at most. The rigid length of such a pump must not be greater than about 35 mm so that the pump can manage to pass through bends of blood vessels. However, the pump may further be prolonged by means of a flexible hose that increases the effective length of the pump.

On the other hand, it is possible to surgically introduce the pump into the heart via the vessel system near the heart. In any case, the pump is small enough to fit into the heart, including the vestibules and the adjacent vascular stumps, and to be operated in the heart without parts of the pump extending from the heart. If any, the catheter connected to the pump is lead out from the heart. This catheter not only includes the lines for supplying electric energy to the pump, but also the signal lines leading from the sensors of the pump to the extracorporeal control unit.

The following is a detailed description of embodiments of the present invention taken in conjunction with the accompanying drawings.

Figure 2:
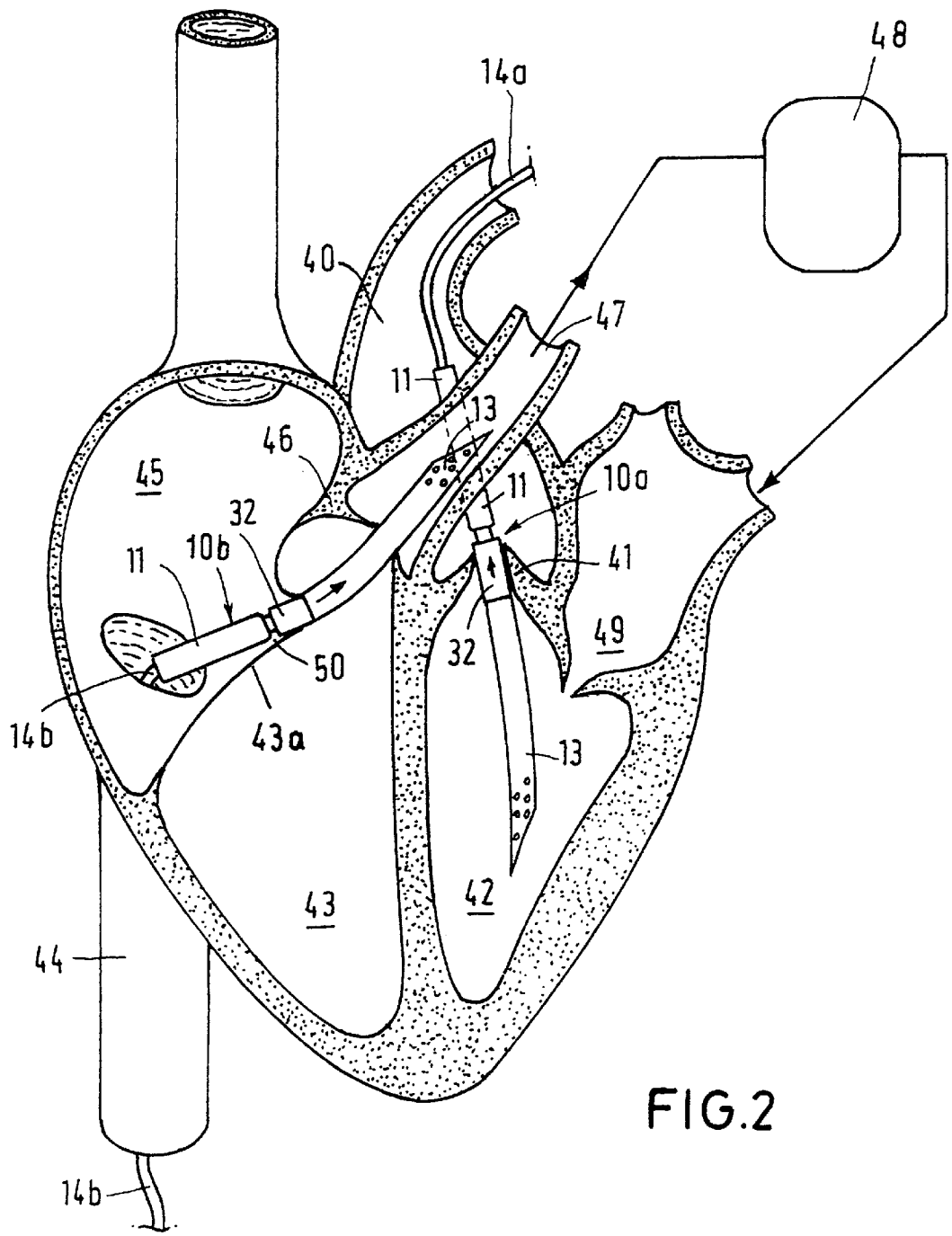
Figure 3:
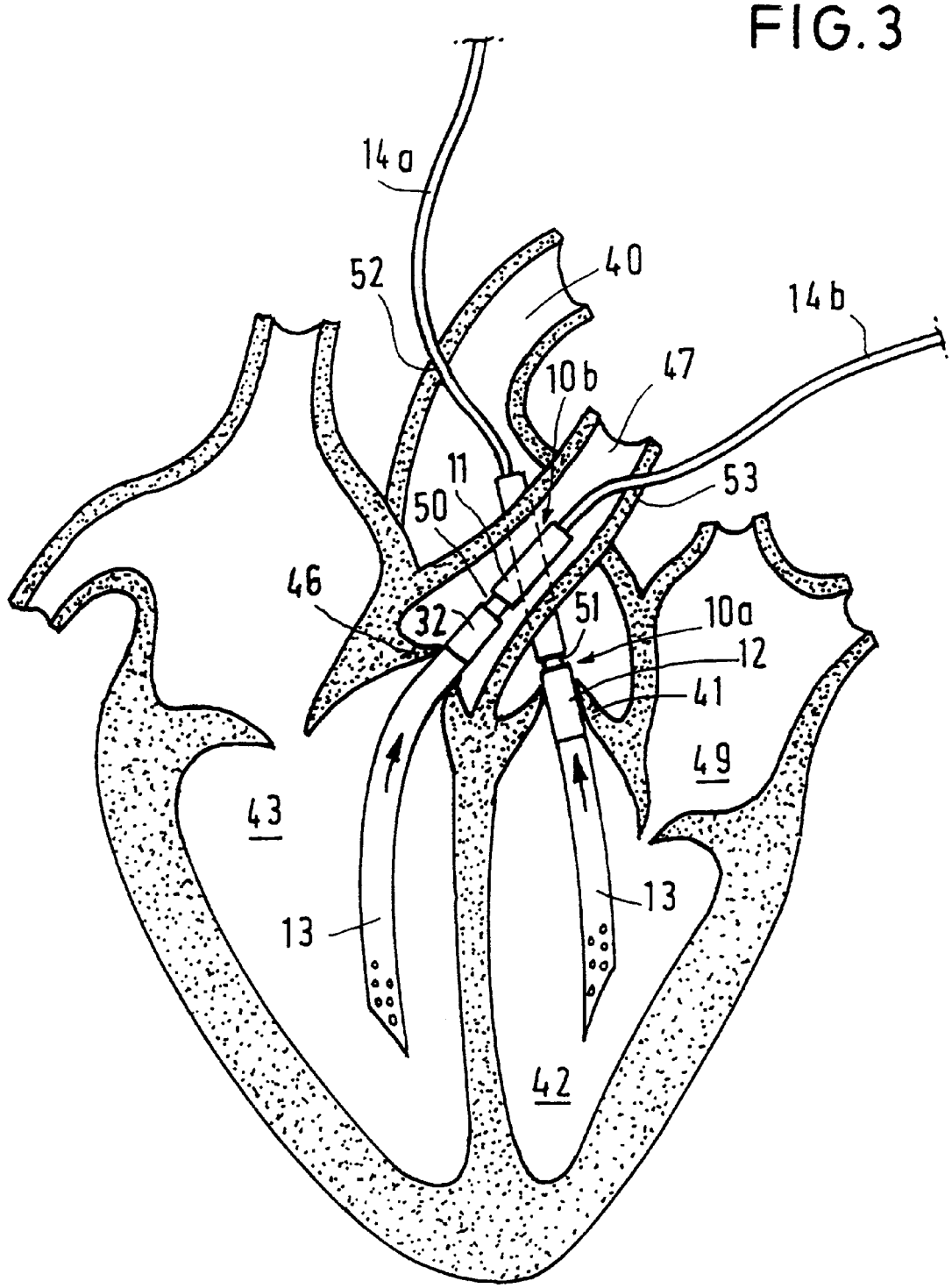
Figure 4:
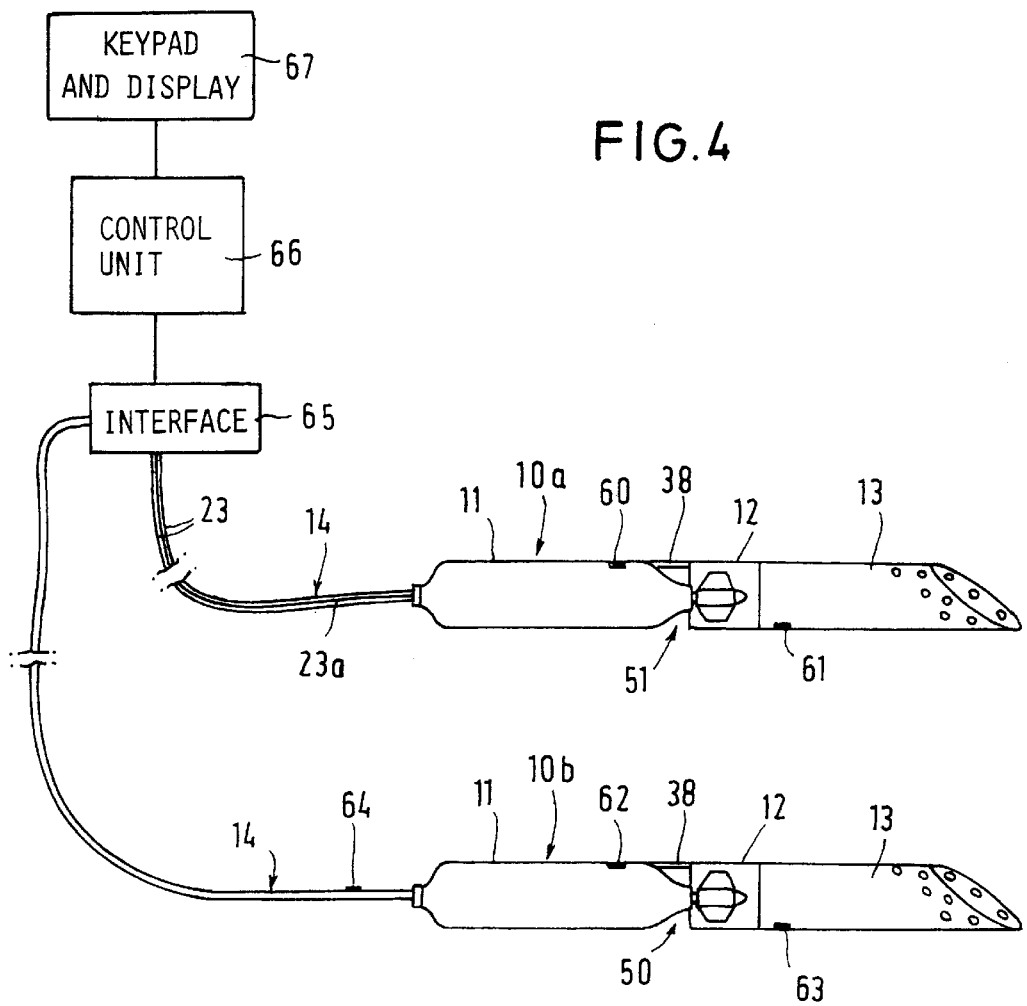
Figure 6:
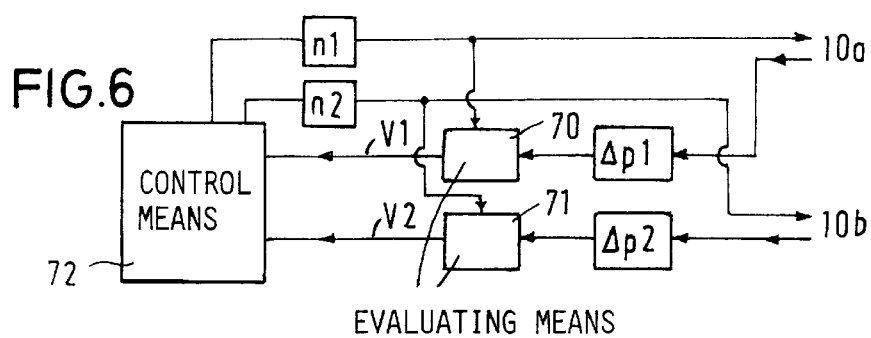
Figure 5:
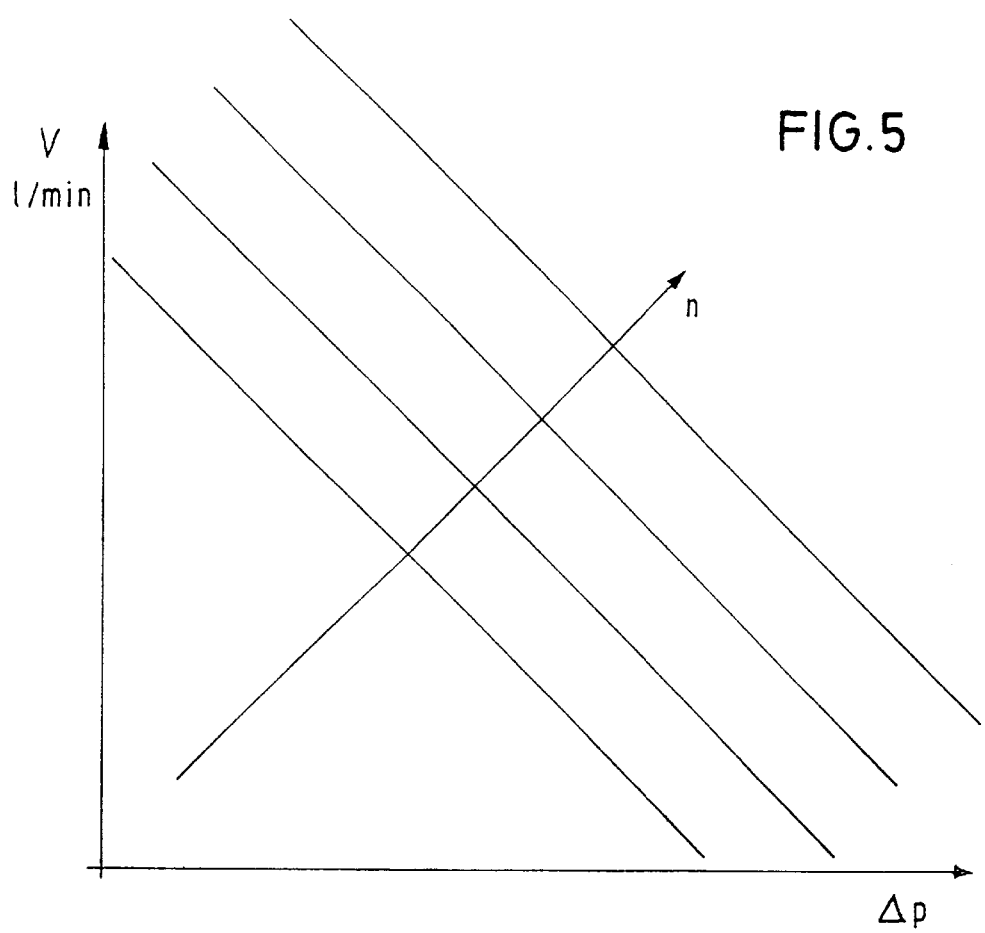
Figure 7:
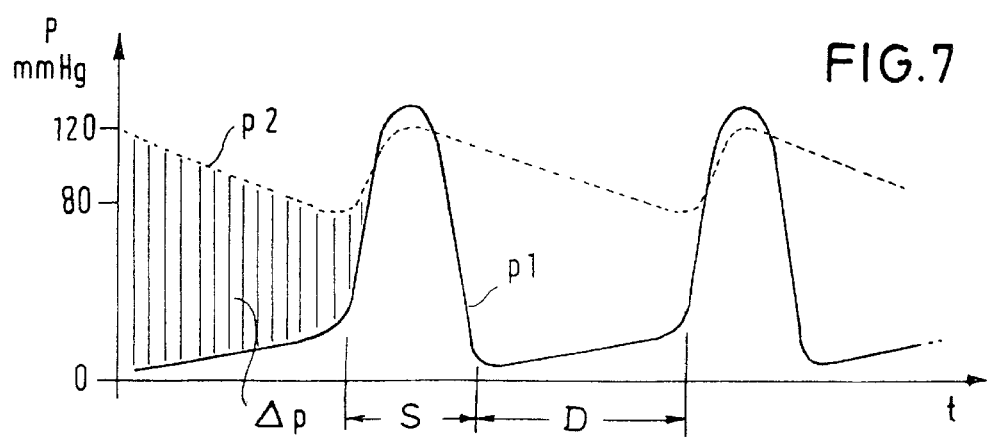

In the Figures:

FIG. 1 illustrates a schematic longitudinal section of one embodiment of an intracardiac blood pump, FIG. 2 shows an embodiment of the intracardiac implementation of two intravascular pumps, FIG. 3 illustrates an embodiment of the implementation of two pumps surgically inserted into the heart via the blood vessel walls, FIG. 4 shows a schematic diagram for explaining the operation of both pumps, FIG. 5 is a diagram for showing the dependance of the volume flow on the differential pressure between the intake side and the delivery side of a pump, FIG. 6 illustrates a block diagram of the control of both pumps, and FIG. 7 is a diagram showing the variation in time of different pressures in the heart.

FIG. 1 shows an intravascular blood pump 10, i.e. a blood pump that may be pushed through the blood vessel system of a patient to eventually arrive in the heart. The outer diameter of such a pump is nowhere larger than 7 mm.

The pump 10 comprises a drive portion 11 and a rigidly connected pump portion 12. The drive portion 11 has an elongate cylindrical housing 20 accommodating an electric motor 21. At the rear end, the housing 20 is closed with an end wall 22 which is followed by a flexible catheter 14 sealing the same. The electric lines 23 for power supply and for controlling the electric motor 21 and further lines 23a connected to the sensors of the pump 10 extend through this catheter 14.

As is typical, the stator 24 of the motor has a plurality of circumferentially distributed coils and a magnetic yoke arranged in the longitudinal direction. It is firmly connected to the motor housing 20. The stator 24 surrounds the rotor 26 that is connected with the motor shaft 25 and is made of permanent magnets magnetized in the active direction. A bearing 27 supports the rear end of the motor shaft in the motor housing or the end wall 22. The motor shaft extends throughout the entire length of the motor housing 20 and projects therefrom to the front.

The front closure of the motor housing is formed by a tubular stationary hub member 30 having its rear end located in a reduced diameter projection 20a of the housing 20. The outer diameter of the hub member tapers towards the front end where a bearing 33 for supporting the motor shaft 25 is situated. This bearing is simultaneously designed as a shaft seal.

The motor shaft 25 protrudes forward from the hub member 30, where it carries an impeller wheel 34 with a hub 35 sitting on the shaft end and blades 36 or pump vanes protruding therefrom and being oblique with respect to the axis of the impeller wheel 34. The impeller wheel 34 is accommodated in a cylindrical pump housing 32 connected with the motor housing 20 by three circumferentially distributed webs 38. The motor housing 20 and the pump housing 32 are rigidly interconnected by means of a ring 38 and have equal outer diameters. The diameter of the pump 10 is nowhere larger than this outer diameter.

When the impeller wheel 34 rotates, blood is drawn through the intake opening 37 of the pump housing 32 and forced rearward in the axial direction in the pump housing 32. Through the annular gap between the pump housing 32 and the motor housing 20, blood flows outward along the hub member 30 to further flow along the motor housing 20. Thereby, the heat generated in the drive is carried away without the blood being damaged by excessively high surface temperatures (above 41° C.) on the motor housing 20.

It is also possible to design the pump portion 12 for the opposite delivery direction, the blood being drawn along the motor housing and being discharged axially at the front end opening 27.

FIG. 2 illustrates an embodiment wherein two generally identical pumps 10a, 10b, configured as illustrated in FIG. 1, are used in a heart to support the heart or as a substitute for the pumping function of the heart when the heart is immobilized. Both pumps 10a, 10b are connected with a catheter 14a, 14b, respectively. They have been placed percutaneously, the catheter 14a of the left cardiac pump 10a extending through the aorta 40 and a hose 13 prolongating the pump 10a being advanced into the left ventricle 42 through the aortic valve 41. Here, the pump portion 12 is prolongated by the flexible hose 13 connected with the pump housing 32, the end and/or the side wall of the hose being provided with openings for blood to enter into the pump 10a. The pump 10a takes in through the hose 13 and delivers blood into the aorta 40, while the aortic valve 41 abuts on the pump housing 32 or the hose 13 from outside. Thus, in the left ventricle 42, the pump 10a is operated as a left heart pump with axial intake.

The other pump 10b is operated as a right heart pump in fluid communication with the right ventricle 43. The catheter 14b passes through the upper or the lower vena cava 44 into the right atrium 45. The hose 13 of the pump 10b projects through the triscupid valve 43a and the pulmonary valve 46 into the pulmonary artery 47 from where the blood flows to the lung 48 for oxygenization. The oxygenized blood flows into the left vestibule 49 and on into the left ventricle 42.

The pump 10b takes in through the radial inlet 50 and conveys blood through the hose 13 axially into the pulmonary artery 47. Thus, the pump 10b is operated inversely to the pump 10a.

Both pumps 10a, 10b are introduced into the heart without one of the ventricles having to be surgically opened.

FIG. 3 illustrates another possibility of positioning two pumps in the heart, with the ability to support the heart or to replace the pumping function of the heart completely. In contrast with FIG. 2, both pumps 10a, 10b have been implanted surgically through incisions made in the vessel system, the catheter 14a of the left heart pump 10a passing through the aorta wall 52, whereas the catheter 14b of the right heart pump 10b penetrating the wall of the pulmonary artery 47 at 53. The hose 13 of the left heart pump 10a is arranged in the left ventricle 42 and enclosed by the aortic valve 41 at the end distal from the outlet opening 51. The hose 13 of the right heart pump 10b is arranged in the right ventricle 43 and surrounded by the pulmonary valve 46. Both pumps 10a, 10b are operated such that they take in through their hoses 13 and deliver through the outlet openings 50 and 51.

FIG. 4 is a schematic illustration of the two pumps 10a, 10b of the previous embodiment with different sensors. Specifically, the outer surface of the drive unit 11 is provided with a first pressure sensor 60 located close to the radial opening 51, whereas a second pressure sensor 61 is arranged near the inlet of the pump housing. The lines 23a of the sensors are integrated into the elements of the pump and extend through the catheter 14 together with the supply lines 23. The sensor surface of the pressure sensor 60 is on the exterior of the motor housing. Conversely, the sensor face of the pressure sensor 61 is provided on the inner surface of the hose 13. Further, a temperature sensor may be provided at the drive portion for monitoring the motor temperature.

Similarly, in the pump 10b, a first pressure sensor 62 is provided on the outer surface of the motor housing and a further pressure sensor 63 is provided on the inner surface of the hose 13. The lines of these sensors also extend through the catheter 14. The catheter 14 is provided with an oxygen sensor 64 providing information on the oxygenation of the blood.

The supply lines 23 and the lines 23a are connected with an extracorporeal interface 65. This interface supplies the signals from the sensors to a control unit 66 that evaluates these signals and controls the pumps 1a, 10b in dependence thereon. A keypad and display device 67 is connected with the control unit 66 to allow for information to be entered and displayed.

Using the information supplied by the sensors, it is possible to determine the position of a pump relative to an external enclosing member, e.g. a cardiac valve. When the pump inlet and the pump outlet are on different sides of the enclosing member, a differential pressure will appear at the pressure sensors due to the different pressure conditions. When the heart beats, this differential pressure also varies in time. On the other hand, equal measured pressure values indicate an incorrect positioning of the pump because both pressure sensors measure the same pressure. The evaluation of the data supplied by the two pressure sensors, with consideration to the motor current, provides important information on the positioning and the operation of the pump. By comparing the differential pressure to the momentaneous motor current, it is also possible to determine blocking conditions or cavitation.

Information on the inlet and outlet pressures of the pump, together with the energy consumption of the electric motor, provide important statements on the functioning of a pump device. They also supply a real time indication on the volume flow and allow for the pump to be positioned without x-ray or ultrasonic control. Moreover, a real time monitoring of an impeded inlet flow can be effected, as may be caused, e.g., by a collapse of the ventricle, thrombogenesis, occlusion of the hose or by cardiac tissue being drawn in. Further, the sensors make it possible to monitor the wear of bearings, of failures of the motor or to predict such events. Furthermore, the operation of the pump can be maintained with acceptable total hemolysis rates for the required period of use and with the required volume flow of 3.6 to 5 l/min. The performance trends of various parameters may be displayed and analyzed for several hours of operation, with alarm conditions that require immediate intervention being detected without necessitating permanent control by personnel. Further, the heart of a patient can be monitored without removing the pump. When placing two instrumented pumps, to supply the control unit with the local information provided by one pump so as to control the operation of the other pump, thereby optimizing the performance of the overall system.

The control unit 66 controls both pumps 10a, 10b such that each pump delivers a certain volume flow (volume of blood per unit time). In doing so, the right heart pump 10b pumps a predetermined percentage of the volume flow of the left heart pump 10a, for example 90%. The volume flow of the right heart pump is always smaller than that of the left heart pump. Primarily, the pumping capacity of the left heart pump 10a is controlled such that a predetermined volume flow is maintained. Subsequently, the pumping capacity of the right heart pump 10b is determined as a function thereof. This is a master-slave operation, where usually the left heart pump 10a is the master and the right heart pump 10b is the slave.

The pumps are driven by synchronous motors, with the control unit 66 supplying the required drive frequency or rotational speed n. The volume flow of each pump is a function of the rotational speed n.

FIG. 5 illustrates the volume flow V of a pump in dependance on the differential pressure ΔP between the intake side and the delivery side of the pump for respective different rotational speeds n. Each parallel straight line relates to a specific rotational speed n. It is evident that the volume flow V may be calculated from the differential pressure ΔP when the rotational speed n is known. The motor 21 is an electronically commutated synchronous motor. Since the rotational speed is preset by the control unit, the rotational speed is known. The differential pressure ΔP is determined by means of the sensors 60 and 61 or 62 and 63, respectively. Moreover, of course, the absolute values of the pressures are measured and evaluated as well.

When a pump takes in through the radial intake opening 50 or 51 and delivers into the hose 13, the pressure at the hose-side pressure sensor 61 or 63 is greater than at the intake-side pressure sensor 60 or 62. However, when the pump pumps in the opposite direction, i.e. when it takes in through the hose 13, the pressure at the pressure sensor 60 or 62 is greater than the pressure at the pressure sensor 61 or 63, respectively.

The diagram of FIG. 6 illustrates how the volume flows V1 and V2 are determined. The differential pressure ΔP1 at the first pump and the differential pressure ΔP2 at the second pump are measured. The rotational sped n1 of the pump 10a and the differential pressure ΔP1 are supplied to a first evaluating means 70. The rotational speed n2 of the second pump 10b and the differential pressure ΔP2 at the second pump are supplied to a second evaluating means 71. Then, according to the diagram of FIG. 5, the evaluating means 70, 71 provide the volume flows V1 and V2 of the first and second pumps to the control means 72, which thereupon sets the rotational speeds n1 and n2 such that the volume flows V1 and V2 take predetermined values. In the embodiment described, the volume flows for both pumps are set in mutual dependance such that the volume flow V2 is 90% of the volume flow V1. The volume flows are maintained or regulated independently for each pump.

It can happen that one of the pumps is entirely or partly occluded by the pump getting sucked to cardiac tissue or the valve apparatus. In this case, the pressure sensors supply abnormal values. The rotational speed of the respective pump will then be reduced for a certain time so that the cardiac tissue may disengage itself, and, subsequently, the rotational speed will be increased again to the desired number. When the measured absolute pressure becomes too high, the control unit 66 will effect a limitation—and, if need be, a reduction—of the volume flow to avoid damage to downstream organs (lungs).

Measuring the pressure also provides a watch function. The pressure in the right ventricle or in the pulmonary artery must not exceed a certain value, and the pressure in the left ventricle or in the aorta must not fall below a certain pressure. When corresponding pressure deviations are detected, an alarm is emitted or an adjustment is effected.

FIG. 7 illustrates the pressure variation p1 in the left ventricle of the beating heart with the systoles S and the diastoles D. One can see a strongly pulsating pressure that drops sharply between systoles S. Moreover, the pressure variation p2 in the aorta is illustrated. The aortic pressure may also pulsate, yet it does so in a much narrower pressure range. The differential pressure ΔP is determined from p2−p1. This differential pressure may be determined with the pressure sensors provided on the pumps.

The sensors 61–63 described above are absolute pressure sensors. It is also possible, to provide the pump housing 32 with a differential pressure sensor in the form of a membrane subjected to a different pressure on its inner side than on its outer side. Thus, the differential pressure may be determined with a single sensor.

Measuring the pressures and the differential pressures is important in particular for the insertion of the pump into the correct position in the heart. The insertion may be done with the pump at a standstill or running at a low rotational speed while the heart is beating. When one pressure sensor detects the strongly pulsating pressure variation p1 and the other detects the weakly pulsating pressure variation p2, the pump is positioned correctly.

However, measuring the pressure is not necessary for positioning. Rather, the positioning may also be monitored by means of the current variation of the pump. As long as the inlet and the outlet of a pump are in the same space, both are subjected to the same pressure. If the pump is driven with a certain rotational speed, the variation in time of the pump current is constant. If, however, the outlet and the inlet of the pump are in different spaces with pressures varying in time, a not smooth, pulsating pump current will be obtained. Thus, it can be determined on the basis of the pump current, whether the cardiac valve correctly encloses the pump housing or the hose so that the inlet of the pump is located in the ventricle or the vestibule and the outlet is in the aorta or the pulmonary artery.

What is claimed is:

1. An intracardiac pump device with two pumps (10a, 10b) to be placed in the heart, each including a drive portion (11) and a pump portion (12) rigidly connected therewith, comprising a common control unit (66) that controls both pumps (10a, 10b) in mutual dependance upon one another such that flow generated by one of said pumps is used to control the operation of the other said pump.

2. The pump device of claim 1, wherein one pump (10a) is a right heart pump for the right ventricle (43) and the other pump (10b) is a left heart pump for the left ventricle (42), and that the volume flows of both pumps are controlled by the common control unit such that the volume flow of the left heart pump (10b) is larger than that of the right heart pump (10b).

3. The pump device of claim 2, characterized in that the volume flow of the left heart pump (10b) is larger by a predetermined percentage, preferably about 10%, than that of the right heart pump (10a).

4. The pump device of claim 1, wherein a volume flow measuring means for determining flow (V) of the respective pump is provided for each pump (10a, 10b), the means communicating with the control unit (66).

5. The pump device of claim 4, wherein the volume flow measuring means comprises at least one differential pressure measuring means determining the differential pressure ($\Delta P1$, $\Delta P2$) between the intake side of the pump and the delivery side, and that means are provided for determining the volume flow (v) from the differential pressure ($\Delta P1$, $\Delta P2$) and the rotational speed of the pump.

6. The pump device of claim 1, wherein the pumps (10a, 10b) each comprise an electric motor driven with alternating current of controllable frequency.

7. The pump of claim 1, wherein at least one absolute pressure sensor (60, 61, 62, 63) is provided at each pump (10a, 10b), the sensor causing a reduction or an increase of the volume flow when the pressure is too high or too low.

8. The pump device of claim 1, wherein the pumps (10a, 10b) are driven under master-slave control, the left heart pump (10a) taking the function of the master and the right pump (10b) following up.

9. The blood pump of claim 1, wherein means are provided for determining which of both pumps (10a, 10b) shows a weaker conveying performance under respective operating conditions and for assigning the master function thereto.

10. The pump device of claim 1, wherein at least one parameter of at least one pump (10a, 10b) is measured and controlled to correspond to a set value.

11. The pump device of claim 10, wherein the parameter is the differential pressure between the intake side and the delivery side of the pump.

12. A method of maintaining total circulatory support normally provided by a heart having a left side, including a left ventricle and left atrium which draws blood from a pair of lungs and pumps into an aorta supplying an arterial vasculature, and a right side, including a right ventricle and right atrium which draws blood from a venous vasculature and pumps into the pair of lungs, comprising the steps of:

percutaneously placing a first intravascular microaxial flow pump through the arterial vasculature into the left ventricle so as to pump blood from the left ventricle into the aorta; and percutaneously placing a second intravascular microaxial flow pump through the venous vasculature into the right ventricle so as to pump blood to the lungs.

13. A method of maintaining total circulatory support normally provided by a heart having a left side, including a left ventricle and left atrium which draws blood from a pair of lungs and pumps into an aorta supplying an arterial vasculature, and a right side, including a right ventricle and right atrium which draws blood from a venous vasculature and pumps into the pair of lungs, comprising the steps of:

surgically placing a first intravascular microaxial flow pump in the left ventricle via an arteriotomy in the aorta so as to pump blood from the left ventricle into the aorta; and surgically placing a second intravascular microaxial flow pump in the right ventricle via a arteriotomy in the pulmonary artery so as to pump blood into the lungs.

* * * * *